(12) United States Patent
Sadahiro (10) Patent No.: US 9,003,871 B2
(45) Date of Patent: Apr. 14, 2015

(54) HARDNESS TESTER AND HARDNESS TEST METHOD

(75) Inventor: Shinichi Sadahiro, Hokkaido (JP)

(73) Assignee: Mitutoyo Corporation, Kanagawa (JP)

( * ) Notice: Subject to any disclaimer, the term of this patent is extended or adjusted under 35 U.S.C. 154(b) by 357 days.

(21) Appl. No.: 13/543,159

(22) Filed: Jul. 6, 2012

(65) Prior Publication Data

US 2013/0125631 A1 May 23, 2013

(30) Foreign Application Priority Data

Nov. 17, 2011 (JP) ................................ 2011-251247

(51) Int. Cl.
*G01N 3/42* (2006.01)
(52) U.S. Cl.
CPC .......... *G01N 3/42* (2013.01); *G01N 2203/0078* (2013.01); *G01N 2203/0647* (2013.01); *G01N 2203/0682* (2013.01)
(58) Field of Classification Search
CPC ............ G01N 2203/0647; G01N 3/42; G01N 2203/0078
USPC .................................................. 73/78, 81, 82
See application file for complete search history.

(56) References Cited

U.S. PATENT DOCUMENTS

| 5,146,779 | A * | 9/1992 | Sugimoto et al. ................. 73/81 |
| 2009/0226033 | A1 * | 9/2009 | Sefcik ............................. 382/103 |
| 2011/0013231 | A1 * | 1/2011 | Hagio ............................. 358/443 |

FOREIGN PATENT DOCUMENTS

| CN | 101839832 | 9/2010 |
| JP | 07-218410 | 8/1995 |
| JP | 08-285755 | 11/1996 |
| JP | 3557765 | 5/2004 |
| JP | 4029832 | 10/2007 |

OTHER PUBLICATIONS

China Office action, dated Aug. 5, 2014 along with an English translation thereof.

* cited by examiner

*Primary Examiner* — Hezron E Williams
*Assistant Examiner* — David Z Huang
(74) *Attorney, Agent, or Firm* — Greenblum & Bernstein, P.L.C.

(57) ABSTRACT

A hardness tester includes an image pickup control section, an indentation region extraction section, an indentation apex extraction section and a hardness calculation section. The image pickup control section obtains picked-up image data of a sample's surface. The region extraction section binarizes the image data, determines based on the binarized image data whether an indentation region candidate is extracted, and when determining that the candidate is not extracted, obtains curvature image data, binarizes the curvature image data, erodes and dilates the binarized curvature image data, performs distance transform on the eroded-and-dilated curvature image data, and extracts a closed region corresponding to the indenter's shape using the distance-transformed curvature image data. The apex extraction section extracts an indentation-measurement-use apex based on the closed region. The hardness calculation section calculates the sample's hardness based on the apex.

11 Claims, 11 Drawing Sheets

HARDNESS TESTER AND HARDNESS TEST METHOD

BACKGROUND OF THE INVENTION

1. Field of the Invention

The present invention relates to a hardness tester and a hardness test method.

2. Description of the Related Art

Conventionally, there is a press-type hardness test method which measures hardness of a sample by pressing an indenter in the shape of a polygonal pyramid onto the surface of the sample, and measuring the lengths of the diagonal lines of a polygonal indentation formed on the surface of the sample. As such a hardness test method, the Vickers hardness test method, the Knoop hardness test method, and the like are well known. The method is often used to evaluate mechanical properties of metallic materials.

As it is well known, the Vickers hardness test method uses an indenter in the shape of a square (or rhombic) pyramid made of diamond, and shows the hardness of a sample from the perspective of a relationship between the average value of the lengths of the two diagonal lines of an indentation in the shape of a square pyramid formed on the surface of the sample and a force (a load) pressed onto the sample by the indenter. The Knoop hardness test method uses an indenter in the shape of a rhombic pyramid (an extended pyramid) made of diamond, and shows the hardness of a sample from the perspective of a relationship between the length of a longer diagonal line of the two diagonal lines of an indentation in the shape of a rhombic pyramid formed on the surface of the sample and a force (a load) pressed onto the sample by the indenter.

Incidentally, a hardness test and tissue observation of a metallic material are often carried out together. In general, in a well-known hardness tester, when a hardness test of a metallic material is carried out, binarization processing is performed on a picked-up image of the surface of a sample picked up by an image pickup section on the basis of determination whether or not a brightness value is less than a predetermined value, so as to extract an indentation region formed on the surface of the sample, which is disclosed by Japanese Patent No. 4029832, for example. However, when a hardness test is carried out after etching processing is performed on the surface of a sample for tissue observation, brightness distribution of a picked-up image of the surface of the sample is complicated, and accordingly, it is hard to recognize an indentation formed on the surface of the sample. As a result, an indentation region cannot be extracted correctly.

Then, in order to solve the abovementioned problem, a technology is disclosed by Japanese Patent No. 3557765, for example. By the technology, images of the surface of a sample are picked up before and after an indentation is formed thereon, and an indentation region is extracted based on a difference between the picked-up image which is picked up before the indentation is formed and the picked-up image which is picked up after the indentation is formed.

SUMMARY OF THE INVENTION

However, the technology disclosed by Japanese Patent No. 3557765 requires two picked-up images of the surface of a sample, and hence processing is complicated. In addition, if the image pickup position differs even a little between before and after an indentation is formed on the surface of a sample, which is caused by the position of an image pickup section being shifted or the like, a proper difference cannot be obtained. As a result, an indentation region cannot be extracted correctly.

Objects of the present invention are to provide a hardness tester and a hardness test method which can correctly and easily extract an indentation region even from a sample on which etching processing is performed.

In order to achieve at least one of the abovementioned objects, according to a first aspect of the present invention, there is provided a hardness tester which applies a predetermined test force with an indenter to a surface of a sample placed on a sample support to form an indentation, and measures a dimension of the indentation to measure hardness of the sample, the hardness tester including: an image pickup control section which controls an image pickup section to pick up an image of the surface of the sample, to obtain picked-up image data of the surface of the sample; an indentation region extraction section which (i) binarizes the picked-up image data, (ii) erodes and dilates the binarized image data, and (iii) performs distance transform on the eroded-and-dilated image data, to extract a closed region corresponding to a shape of the indenter using the distance-transformed image data; an indentation apex extraction section which extracts an indentation-measurement-use apex on the basis of the extracted closed region, the apex being used to measure the dimension of the indentation; and a hardness calculation section which calculates the hardness of the sample on the basis of the extracted apex, wherein the indentation region extraction section determines on the basis of the binarized image data whether an indentation region candidate is extracted, and when determining that the indentation region candidate is not extracted, (i) obtains curvature image data on the basis of a brightness value of the picked-up image data, (ii) binarizes the obtained curvature image data, and (iii) erodes and dilates the binarized curvature image data.

In order to achieve at least one of the abovementioned objects, according to a second aspect of the present invention, there is provided a hardness tester which applies a predetermined test force with an indenter to a surface of a sample placed on a sample support to form an indentation, and measures a dimension of the indentation to measure hardness of the sample, the hardness tester including: an image pickup control section which controls an image pickup section to pick up an image of the surface of the sample, to obtain picked-up image data of the surface of the sample; an indentation region extraction section which obtains curvature image data on the basis of a brightness value of the picked-up image data, and extracts a flat part where a curvature is less than a predetermined value as an indentation region referring to the obtained curvature image data; and a hardness calculation section which calculates the hardness of the sample on the basis of the indentation region.

In order to achieve at least one of the abovementioned objects, according to a third aspect of the present invention, there is provided a hardness test method which applies a predetermined test force with an indenter to a surface of a sample placed on a sample support to form an indentation, and measures a dimension of the indentation to measure hardness of the sample, the hardness test method including: an image pickup control step of controlling an image pickup step to pick up an image of the surface of the sample, to obtain picked-up image data of the surface of the sample; an indentation region extraction step of (i) binarizing the picked-up image data, (ii) eroding and dilating the binarized image data, and (iii) performing distance transform on the eroded-and-dilated image data, to extract a closed region corresponding to a shape of the indenter using the distance-transformed image data; an indentation apex extraction step of extracting an indentation-measurement-use apex on the basis of the extracted closed region, the apex being used to measure the dimension of the indentation; and a hardness calculation step of calculating the hardness of the sample on the basis of the extracted apex, wherein in the indentation region extraction step, whether an indentation region candidate is extracted is determined on the basis of the binarized image data, and when that the indentation region candidate is not extracted is determined, (i) curvature image data is obtained on the basis of a brightness value of the picked-up image data, (ii) the obtained curvature image data is binarized, and (iii) the binarized curvature image data is eroded and dilated.

In order to achieve at least one of the abovementioned objects, according to a fourth aspect of the present invention, there is provided a hardness test method which applies a predetermined test force with an indenter to a surface of a sample placed on a sample support to form an indentation, and measures a dimension of the indentation to measure hardness of the sample, the hardness test method including: an image pickup control step of controlling an image pickup step to pick up an image of the surface of the sample, to obtain picked-up image data of the surface of the sample; an indentation region extraction step of obtaining curvature image data on the basis of a brightness value of the picked-up image data, and extracting a flat part where a curvature is less than a predetermined value as an indentation region referring to the obtained curvature image data; and a hardness calculation step of calculating the hardness of the sample on the basis of the indentation region.

BRIEF DESCRIPTION OF THE DRAWINGS

The present invention will become more fully understood from the detailed description given hereinbelow and the accompanying drawings which are given by way of illustration only, and thus are not intended as definitions of limits of the present invention, wherein.

DESCRIPTION OF THE PREFERRED EMBODIMENTS

In the following, an embodiment of the present invention is described referring to the accompanying drawings. In the following, an X direction, a Y direction and a Z direction shown in FIG. 1 respectively represent a right-left direction, a front-back direction and an up-down direction. In addition, an X-Y plane represents a horizontal plane.

Figure 1:
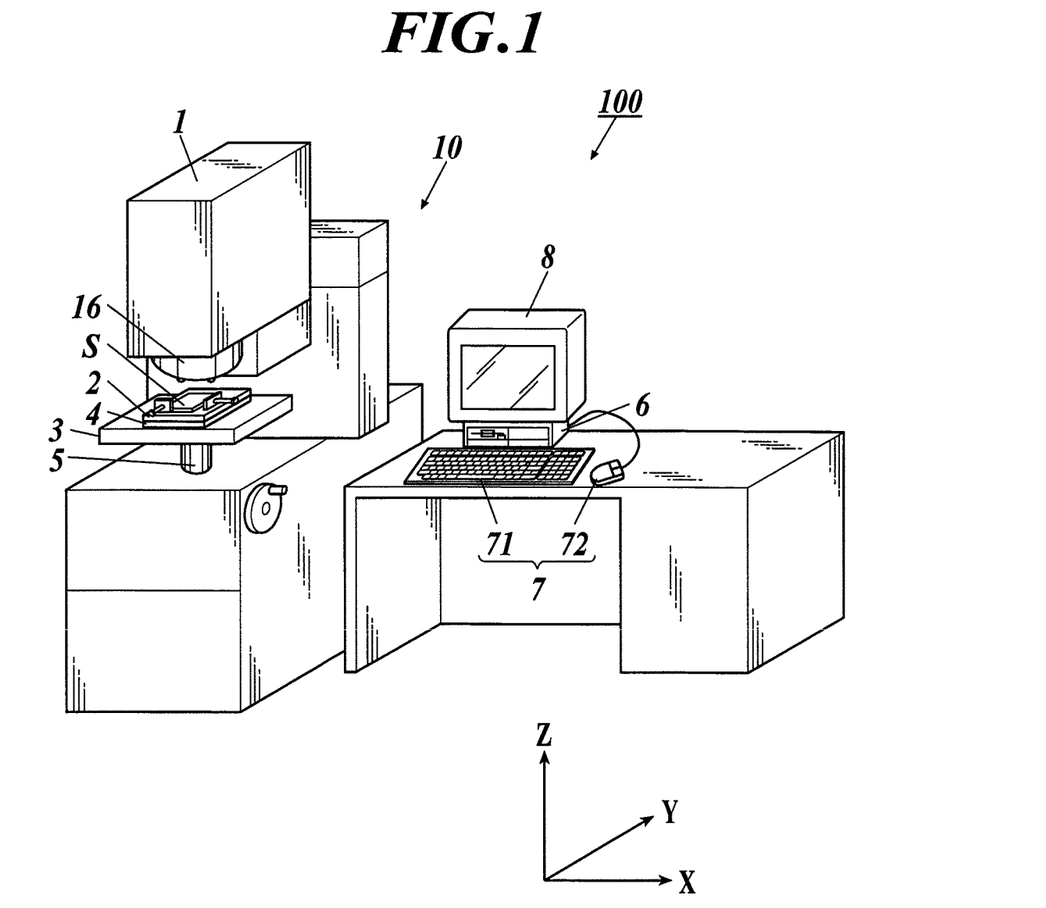
FIG. 1 is a perspective view showing an overall configuration of a hardness tester in accordance with an embodiment of the present invention.
Figure 2:
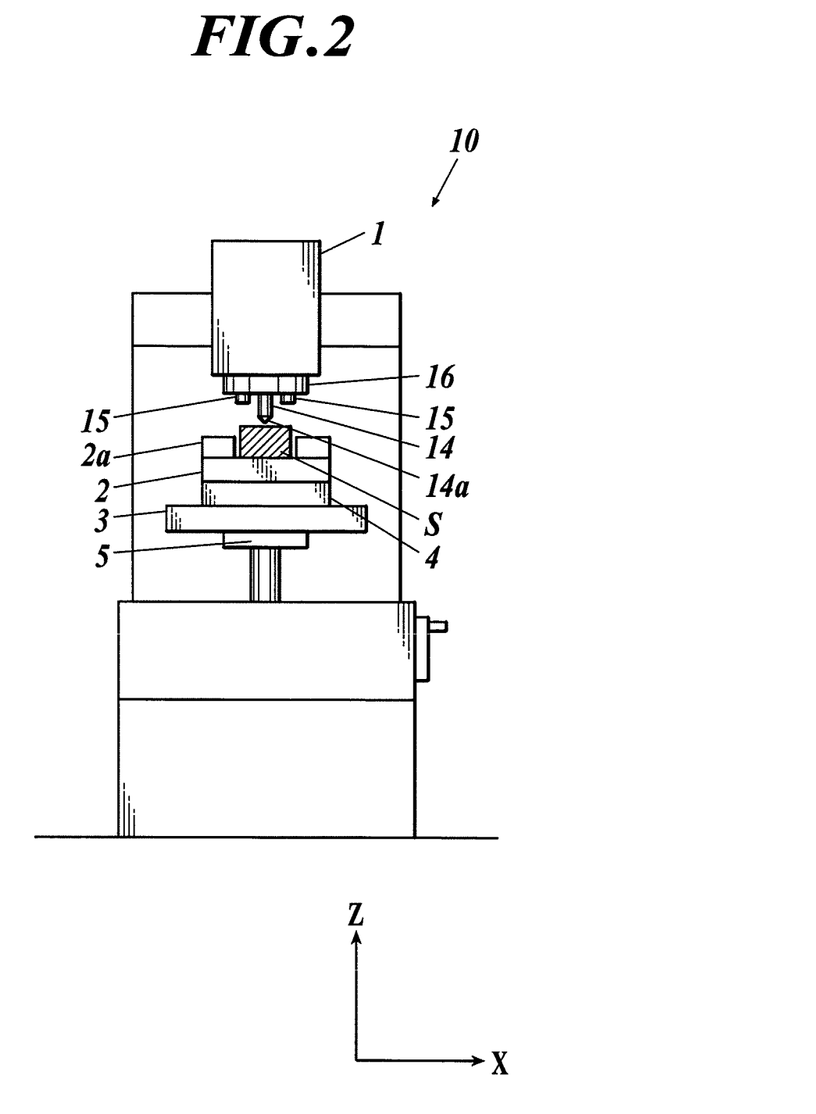
FIG. 2 is a schematic diagram showing a tester main body of the hardness tester.

A hardness tester 100 is a Vickers hardness tester which includes an indenter 14a in the shape of a rhombic pyramid. As shown in FIGS. 1 and 2, the hardness tester 100 includes a tester main body 10, a control section 6, an operation section 7, and a monitor 8.

The tester main body 10 includes a hardness measurement section 1 which measures the hardness of a sample S, a sample support 2 on which the sample S is placed, an XY stage 3 which moves the sample support 2, an AF stage 4 with which the surface of the sample S is in focus, and an up-down mechanism section 5 which moves the sample support 2 (the XY stage 3 and the AF stage 4) up and down.

Figure 3:
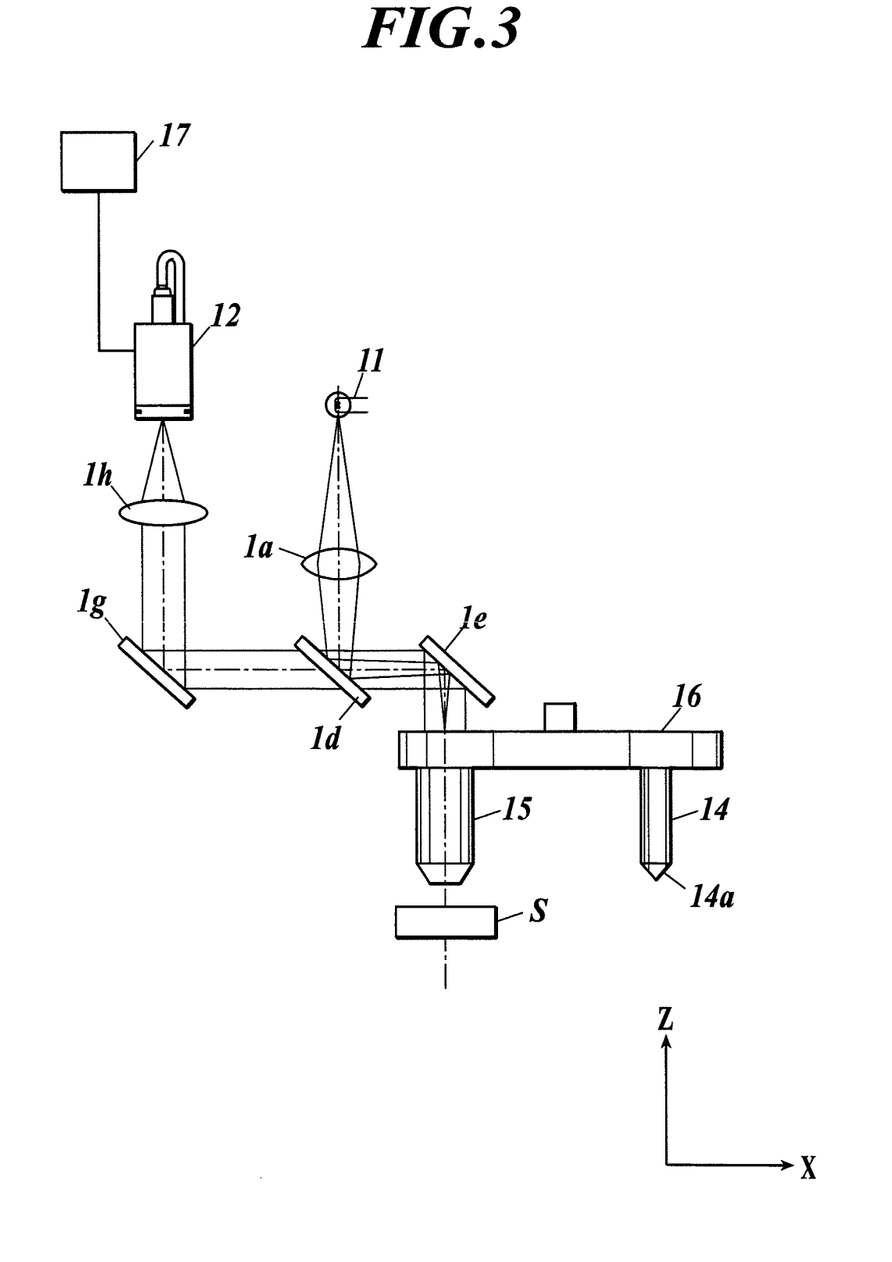
FIG. 3 is a schematic diagram showing a hardness measurement section of the hardness tester.

As shown in FIG. 3, the hardness measurement section 1 includes an illuminator 11 which illuminates the surface of the sample S, a CCD camera 12 which picks up an image of the surface of the sample S, and a turret 16. The turret 16 is provided with object lenses 15 and an indenter shaft 14 provided with the indenter 14a, and rotates in such a way that the indenter shaft 14 (i.e. the indenter 14a) or any one of the object lenses 15 is positioned above the sample S.

The illuminator 11 illuminates the surface of the sample S by emitting light. The light emitted from the illuminator 11 reaches the surface of the sample S via a lens 1a, a half mirror 1d, a mirror 1e, and one of the object lenses 15.

The CCD camera 12 picks up an image of the surface of the sample S and an indentation formed on the surface of the sample S so as to obtain image data thereof on the basis of reflected light entered from the surface of the sample S via one of the object lenses 15, the mirror 1e, the half mirror 1d, a mirror 1g, and a lens 1h, and outputs the obtained image data to the control section 6 via a frame grabber 17. The frame grabber 17 can store and accumulate image data of a plurality of frames at a time.

Thus, the CCD camera 12 functions as an image pickup section.

The indenter shaft 14 is moved to the sample S placed on the sample support 2 by a load mechanism section (not shown) which is driven in accordance with a control signal outputted by the control section 6, and presses the indenter 14a disposed at one end (the tip end) of the indenter shaft 14 onto the surface of the sample S with a predetermined test force.

The object lenses 15 are condensing lenses having different magnifications. The object lenses 15 are held on the underside (undersurface) of the turret 16. Any of the object lenses 15 is positioned above the sample S by rotation of the turret 16 so as to uniformly illuminate the surface of the sample S with the light emitted from the illuminator 11.

The indenter shaft 14 and the object lenses 15 are mounted on the underside of the turret 16. The turret 16 rotates having the Z direction as a rotation center, thereby positioning the indenter shaft 14 or one of the object lenses 15 above the sample S. That is, positioning the indenter shaft 14 above the sample S makes it possible to form an indentation on the surface of the sample S, and positioning one of the object lenses 15 above the sample S makes it possible to observe the formed indentation.

The sample support 2 fixes the sample S, which is placed on the upper-side thereof, thereon with a sample fixing section 2a.

The XY stage 3 is driven by a drive mechanism section (not shown) which is driven in accordance with a control signal outputted by the control section 6, and moves the sample support in a direction (the X direction or the Y direction) perpendicular to a moving direction (the Z direction) of the indenter 14a. The AF stage 4 is driven in accordance with a control signal outputted by the control section 6, and moves the sample support 2 up and down finely on the basis of the image data of the image picked up by the CCD camera 12 so that the surface of the sample S is in focus.

The up-down mechanism section 5 is driven in accordance with a control signal outputted by the control section 6, and moves the sample support 2 (the XY stage 3 and the AF stage 4) in the up-down direction, so as to change a relative distance between the sample support 2 and the object lenses 15.

The operation section 7 includes a keyboard 71 and a mouse 72, and allows a user to make an input operation to carry out a hardness test. When a predetermined input operation is made with the operation section 7, a predetermined operation signal corresponding to the input operation is outputted to the control section 6.

More specifically, the operation section 7 allows a user to choose a condition to determine a focal position for an indentation with the keyboard 71, the mouse 72 or the like.

Furthermore, the operation section 7 allows a user to specify a range within which the sample support 2 (the up-down mechanism section 5 and the AF stage 4) can move, namely, to specify a range of relative distances between the sample support 2 and the object lenses 15.

Still further, the operation section 7 allows a user to input test condition values used for a hardness test carried out by the hardness tester 100. The inputted test condition values are sent to the control section 6. The test condition values are, for example, values of material properties of the sample S, a test force (N) applied to the sample S by the indenter 14a, the magnifications of the object lenses 15, and the like.

Yet further, the operation section 7 allows a user to choose either a manual mode in which the focal position for an indentation is decided manually or an automatic mode in which the focal position for an indentation is decided automatically.

The monitor 8 is constituted of a display device such as an LCD (Liquid Crystal Display), and displays setting conditions for a hardness test inputted with the operation section 7, a result of the hardness test, the image of the surface of the sample S and the indentation formed on the surface of the sample S picked up by the CCD camera 12, and the like. Thus, the monitor 8 functions as a display section.

Figure 4:
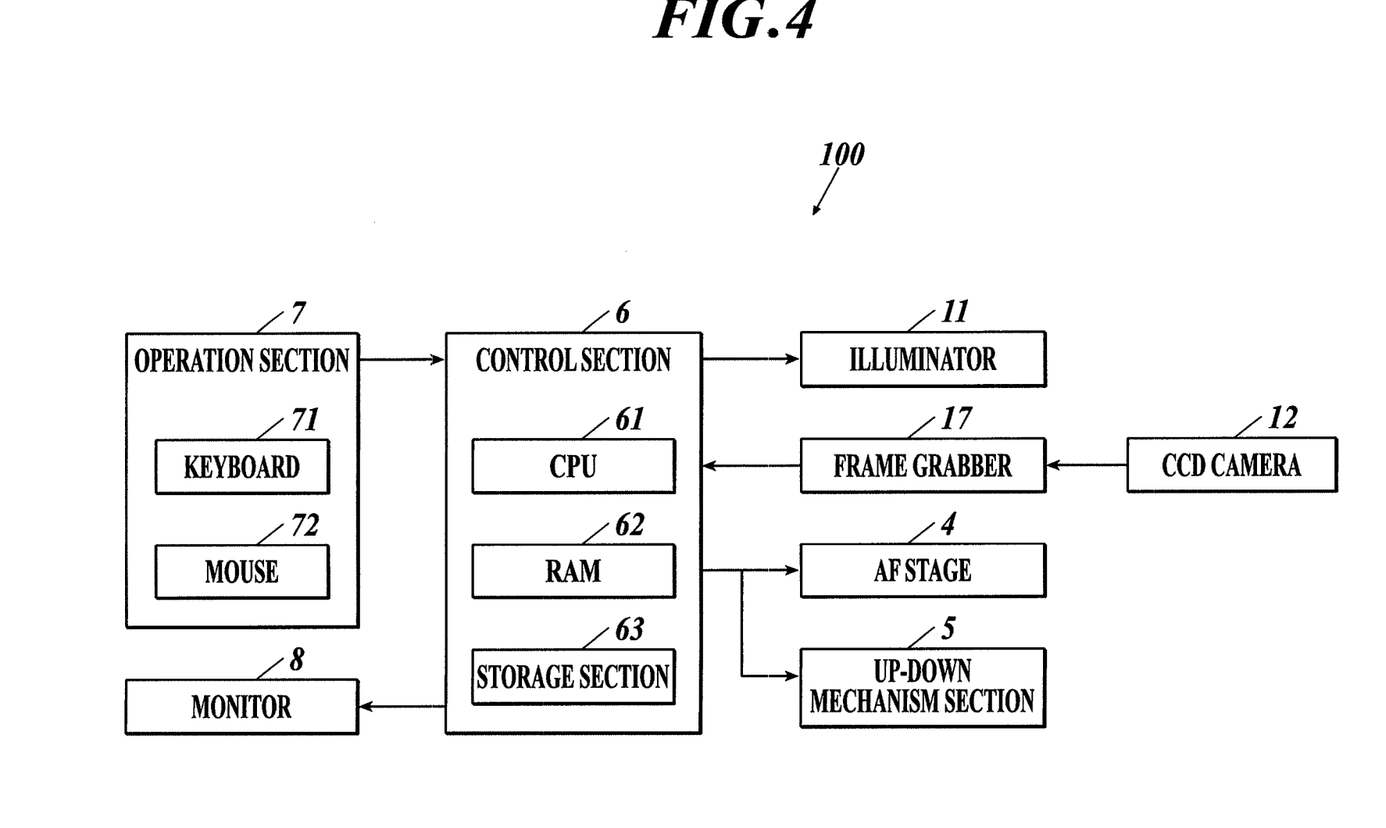
FIG. 4 is a block diagram showing a control configuration of the hardness tester.

As shown in FIG. 4, the control section 6 includes a CPU (Central Processing Unit) 61, a RAM (Random Access Memory) 62, and a storage section 63. The control section 6 has a function to perform operation control to carry out a predetermined hardness test or the like by executing predetermined programs stored in the storage section 63.

The CPU 61 reads a processing program or the like stored in the storage section 63, and loads the read processing program into the RAM 62, so as to perform processing, thereby controlling the hardness tester 100 overall.

The RAM 62 decompresses the processing program or the like executed by the CPU 61 in a program storage region of the RAM 62. Furthermore, the RAM 62 stores input data, a processing result obtained by the processing program or the like being executed, and the like in a data storage region of the RAM 62.

The storage section 63 includes a recording medium (not shown) which stores programs, data, and the like. The recording medium is constituted of a semiconductor memory or the like. The storage section 63 stores various data and various processing programs to realize a function with which the CPU 61 controls the hardness tester 100 overall, data processed by the programs being executed, and the like. More specifically, the storage section 63 stores an XY stage control program, an autofocus program, an indentation forming program, an indentation image pickup control program, an indentation region extraction program, an indentation apex extraction program, a hardness calculation program, a display control program, and the like.

Next, operations of the hardness tester 100 in the embodiment are described.

First, the CPU 61 executes the XY stage control program stored in the storage section 63, so as to move the XY stage 3 in such a way that a predetermined region of the surface of the sample S is positioned just under the CCD camera 12.

Next, the CPU 61 executes the autofocus program stored in the storage section 63, so as to move the AF stage 4 up and down on the basis of the image data (picked-up image data) obtained by the CCD camera 12 of the hardness measurement section 1 so that the surface of the sample S is automatically in focus.

Then, the CPU 61 executes the indentation forming program stored in the storage section 63, so as to form an indentation by pressing the indenter 14a onto the surface of the sample S with a predetermined test force.

Figure 5:
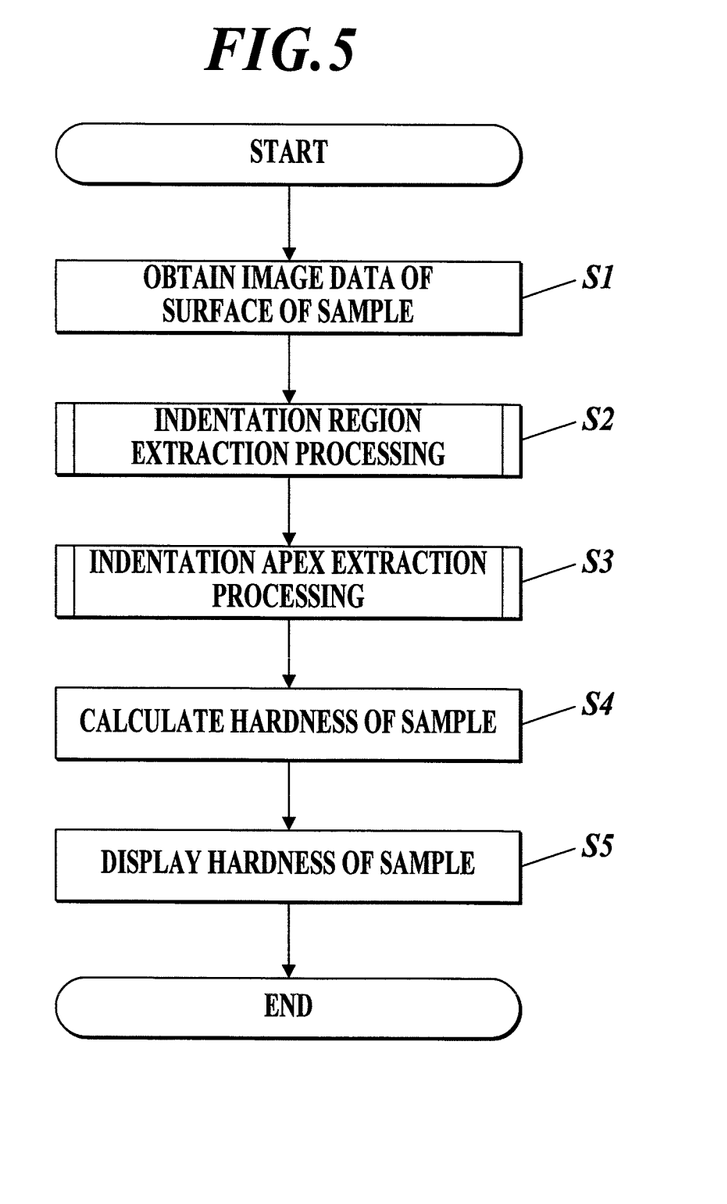
FIG. 5 is a flowchart showing operations of the hardness tester after an indentation is formed.
Figure 7:
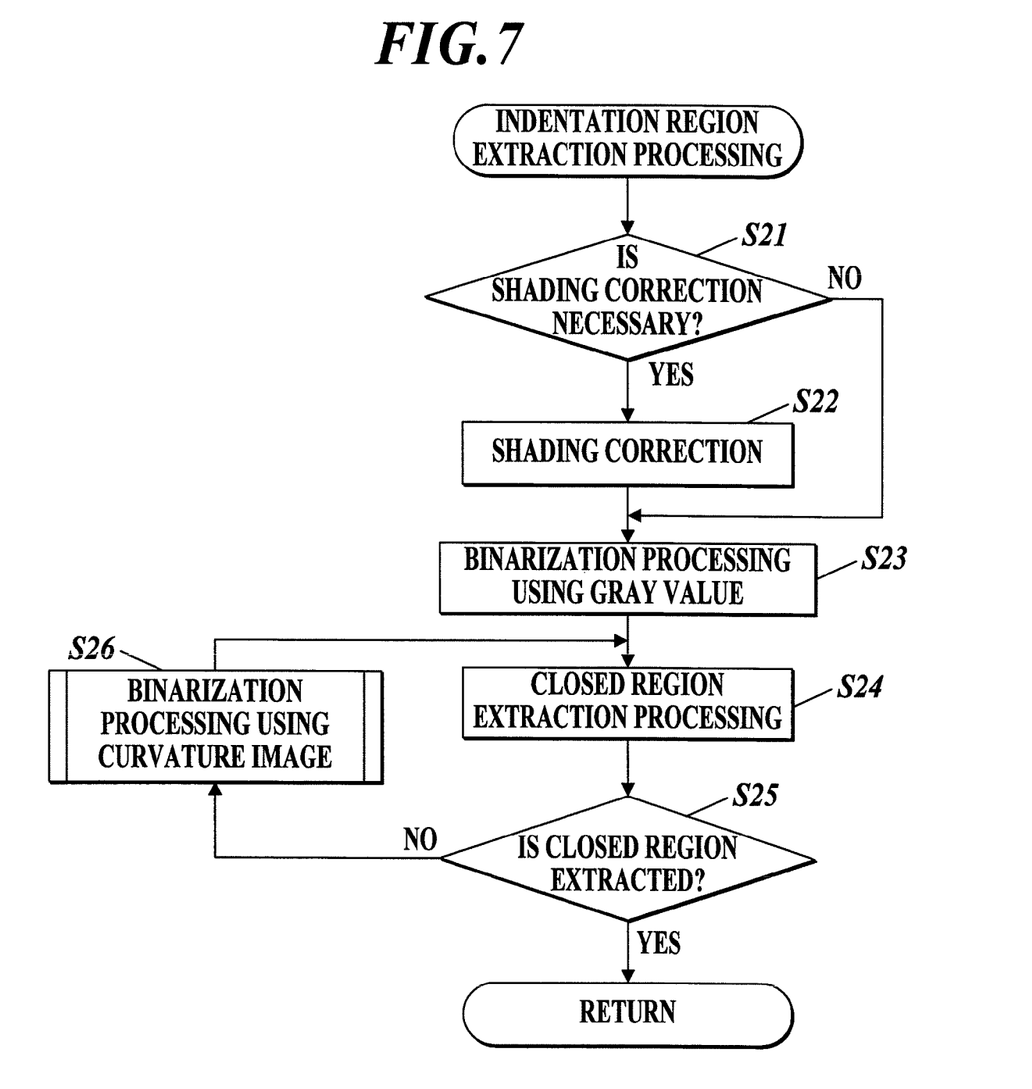
FIG. 7 is a flowchart of indentation region extraction processing performed by the hardness tester.
Figure 8:
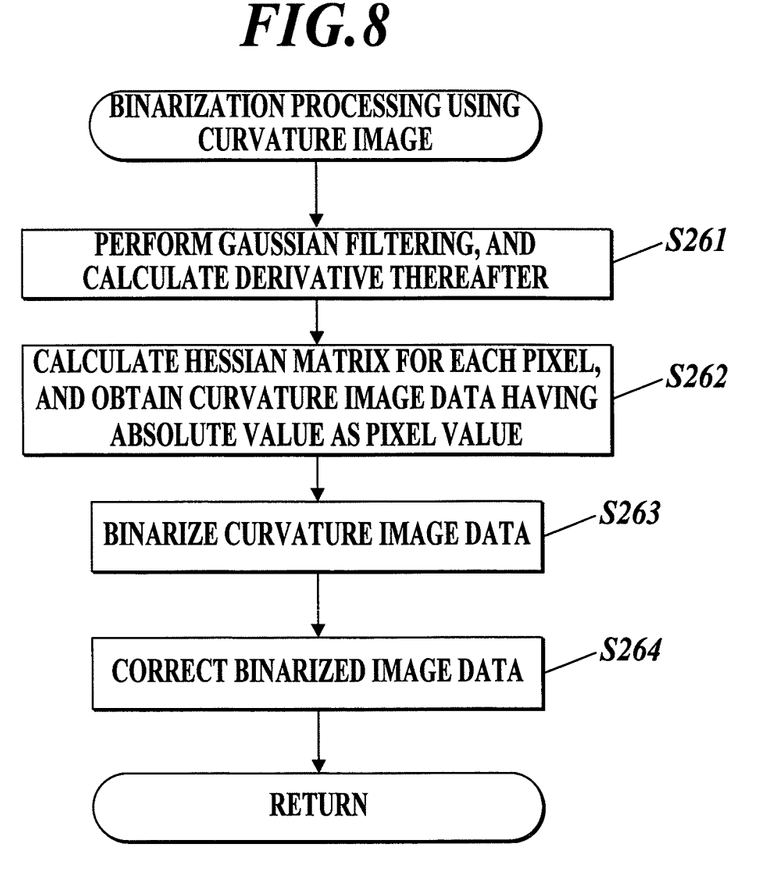
FIG. 8 is a flowchart of binarization processing performed by the hardness tester, using an image having a curvature (i.e. a curvature image or a curved image, hereinbelow)

Next, operations of the hardness tester 100 in the embodiment after an indentation is formed are described, referring to flowcharts of FIGS. 5, 7 and 8. Processing shown in FIGS. 5, 7 and 8 is performed by the CPU 61 executing the programs stored in the storage section 63. In the embodiment, etching processing is performed on the surface of the sample S.

Figure 6:
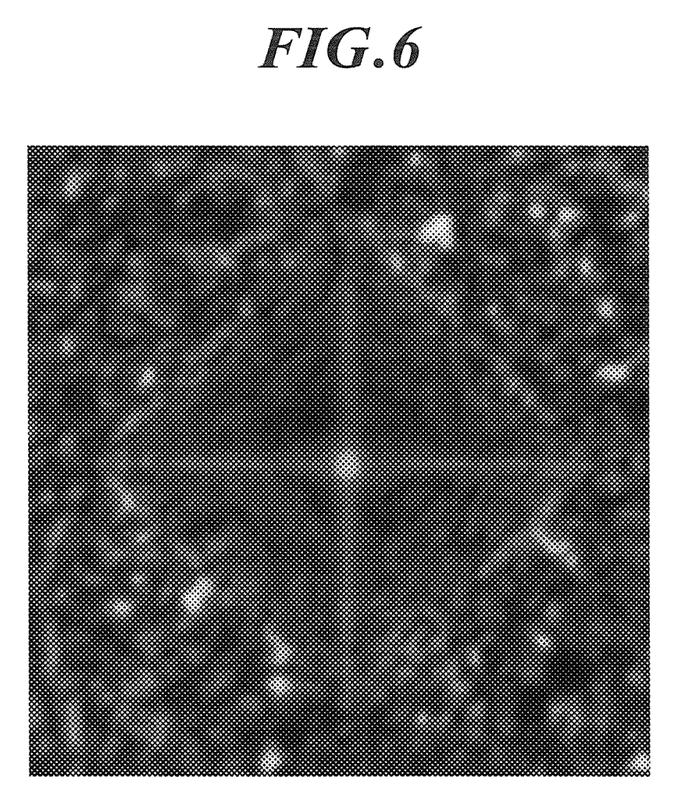
FIG. 6 shows an example of a picked-up image of the surface of a sample S on which etching processing is performed.

First, the CPU 61 executes the image pickup control program stored in the storage section 63, so as to control the CCD camera 12 to pick up an image of the surface of the sample S, thereby obtaining image data (picked-up image data) of the surface of the sample S (Step S1: an image pickup control step). In the embodiment, because the etching processing is performed on the surface of the sample S, as shown in FIG. 6, the image data in which an indentation region and the background are difficult to be distinguished is obtained.

Next, the CPU 61 executes the indentation region extraction program stored in the storage section 63, so as to extract the region of the indentation (the indentation region) formed on the surface of the sample S on the basis of the image data of the surface of the sample S obtained at Step S1 (Step S2: an indentation region extraction step).

More specifically, as shown in FIG. 7, first, the CPU 61 refers to the image data of the surface of the sample S obtained at Step S1 in FIG. 5, and determines whether or not shading correction is necessary to be performed thereon (Step S21). The shading correction is processing to correct uneven brightness of an image caused by the properties of an optical system and/or an image pickup system, so as to obtain the image having even brightness. The determination at Step S21 is made by determining whether or not, on the basis of difference of brightness values of small regions at four corners of the image data, dispersion of the brightness values of the small regions is equal to or more than a predetermined value. When determining that the shading correction is necessary (Step S21; YES), the CPU 61 performs the shading correction on the image data of the surface of the sample S (Step S22), and then moves to Step S23. On the other hand, when determining that the shading correction is unnecessary (Step S21; NO), the CPU 61 moves to Step S23 without performing the shading correction.

Next, the CPU 61 performs binarization processing using a gray value on the image data of the surface of the sample S, the image data being obtained at Step S1 in FIG. 5 or undergoing the shading correction at Step S22 (Step S23). More specifically, the CPU 61 converts the image data of an original image (the image of the surface of the sample S) which is a black-and-white grayscale image into image data having two gradations, namely, black and white. That is, if, for example, the brightness value (lightness) of a pixel of the original image is more than a predetermined threshold value, the CPU 61 replaces the gradation of the pixel with black, and when the brightness value of a pixel is less than the predetermined threshold value, the CPU 61 replaces the gradation of the pixel with white. Consequently, the obtained image data of the surface of the sample S is displayed in such a way that the part replaced with black by the binarization processing is blacker than its corresponding part of the original image, and the part replaced with white by the binarization processing is whiter than its corresponding part of the original image. For example, the brightness values of the pixels of the indentation region of the indentation formed on the surface of the sample S are lower than those of the pixels of the background, and hence the indentation region is displayed by white pixels. The image data binarized (binarized image data) at Step S23 is stored in the storage section 63.

Then, the CPU 61 generates copy data of the image data binarized at Step S23, and erodes and dilates the binarized image data using the copy data of the binarized image data. Furthermore, the CPU 61 performs distance transform on the eroded-and-dilated image data. As for the erosion, the dilation and the distance transform, well-known technologies or technologies proposed by the present inventor in Japanese Patent Application No. 2011-201305 can be used. Hence, detailed description thereof is omitted.

Next, the CPU 61 extracts a closed region (closed region extraction processing) corresponding to the shape of the indenter 14a, using the binarized image data undergoing the distance transform (distance-transformed image data) at Step S23 or binarized image data undergoing distance transform (distance-transformed image data) at Step S264 in FIG. 8 described below (Step S24). As for the extraction of the closed region, a well-known technology or a technology proposed by the present inventor in Japanese Patent Application No. 2011-201305 can be used. Hence, detailed description thereof is omitted.

Next, the CPU 61 determines whether or not the closed region is extracted by the closed region extraction processing performed at Step S24 (Step S25). That is, the CPU 61 determines whether or not the closed region as an indentation region candidate is extracted, on the basis of the binarized image data. The indentation region candidate is a region which is a candidate for the indentation region formed on the surface of the sample S. More specifically, the determination at Step S25 is made by determining whether or not one or more closed regions are stored in the storage section 63. When determining that one or more closed regions are stored in the storage section 63, namely, determining that the closed region is extracted (Step S25; YES), the CPU 61 ends the indentation region extraction processing, and moves to Step S3 in FIG. 5. On the other hand, when determining that one or more closed regions are not stored in the storage section 63, namely, determining that the closed region is not extracted (Step S25; NO), the CPU 61 performs binarization processing using a curvature image (Step S26).

More specifically, as shown in FIG. 8, first, the CPU 61 performs Gaussian filtering on the brightness values of the image data of the surface of the sample S obtained at Step S1 in FIG. 5, and then calculates derivatives of the Gaussian-filtered image data (Step S261). The Gaussian filtering is processing to smooth the brightness values of an image in order to reduce noise of the image by calculating a rate using the function of Gaussian distribution in such a way that the closer a pixel is to a remarkable pixel, the more a weight therefor is, namely, in such a way that the further a pixel is from a remarkable pixel, the less a weight therefor is. The weight is used to calculate the average value of the brightness values. If the Gaussian filter is represented by G, and the image data of the surface of the sample S is represented by I, a derivative A is expressed by the following first formula.

$$A = \frac{\partial^2(G*I)}{\partial x \partial x}, \frac{\partial^2(G*I)}{\partial x \partial y}, \frac{\partial^2(G*I)}{\partial y \partial y} \qquad \text{[First Formula]}$$

Next, the CPU 61 calculates a Hessian matrix H for each pixel of the image data (on a pixel basis) using the derivative A calculated at Step S261, and obtains a curvature image data having the absolute value of the Hessian matrix H as the pixel value (Step S262). The Hessian matrix H is expressed by the following second formula.

$$H = \det\begin{pmatrix} \frac{\partial^2(G*I)}{\partial x \partial x} & \frac{\partial^2(G*I)}{\partial x \partial y} \\ \frac{\partial^2(G*I)}{\partial x \partial y} & \frac{\partial^2(G*I)}{\partial y \partial y} \end{pmatrix} \qquad \text{[Second Formula]}$$

Figure 9:
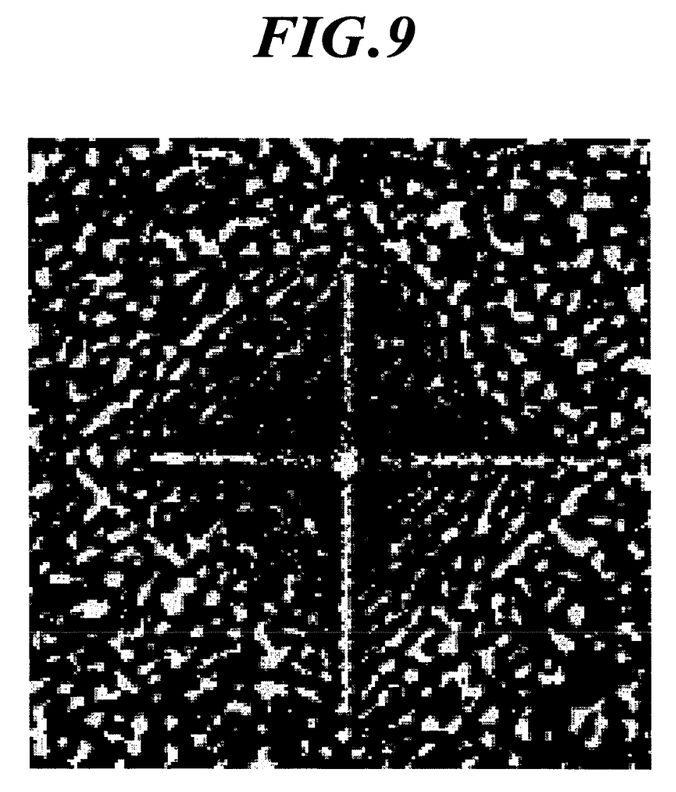
FIG. 9 shows an example of a curvature image obtained by the binarization processing shown in FIG. 8.

As a result of Step S262, the curvature image data shown in FIG. 9 can be obtained, for example.

Figure 10:
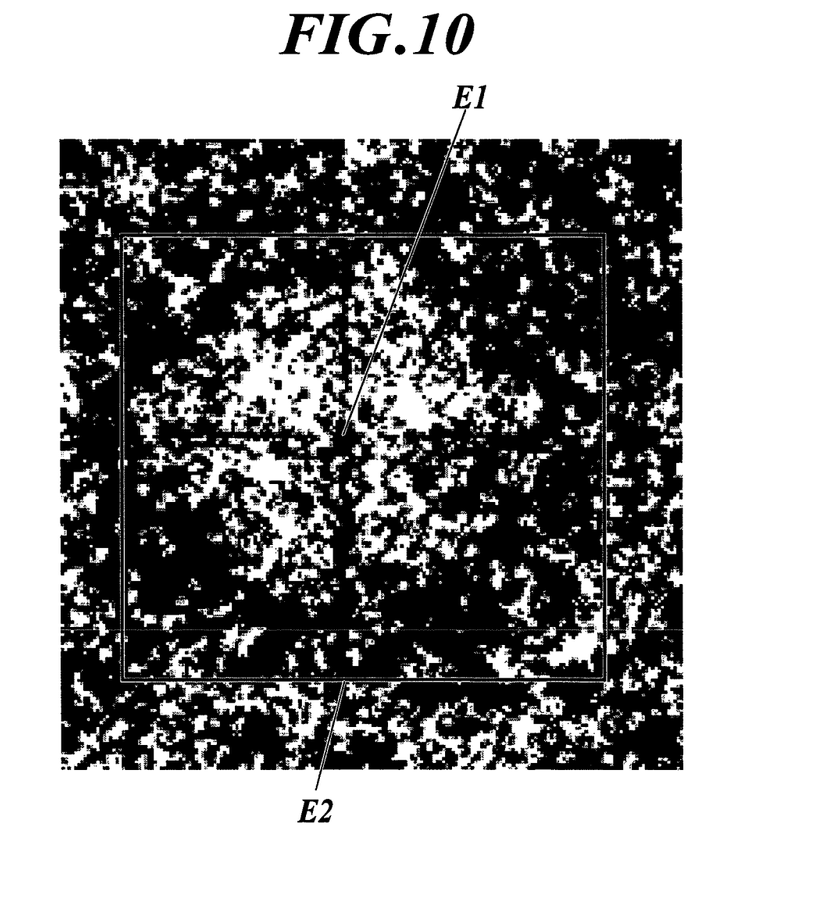
FIG. 10 shows an example of an image obtained by binarizing the curvature image shown in FIG. 9.

Next, the CPU 61 binarizes the curvature image data obtained at Step S262 (Step S263). More specifically, the CPU 61 converts the curvature image data, which is a black-and-white grayscale image, into image data having two gradations, namely, black and white. That is, if the pixel value (the magnitude of the absolute value of a curvature) of a pixel of the curvature image data is more than a predetermined threshold value, the CPU 61 replaces the pixel with black, and if the pixel value of a pixel thereof is less than the predetermined threshold value, the CPU 61 replaces the gradation of the pixel with white. For example, the indentation region formed on the surface of the sample S has a curvature which is less than that of the background. Hence, as shown in FIG. 10, the indentation region is displayed by white pixels.

Figure 11:
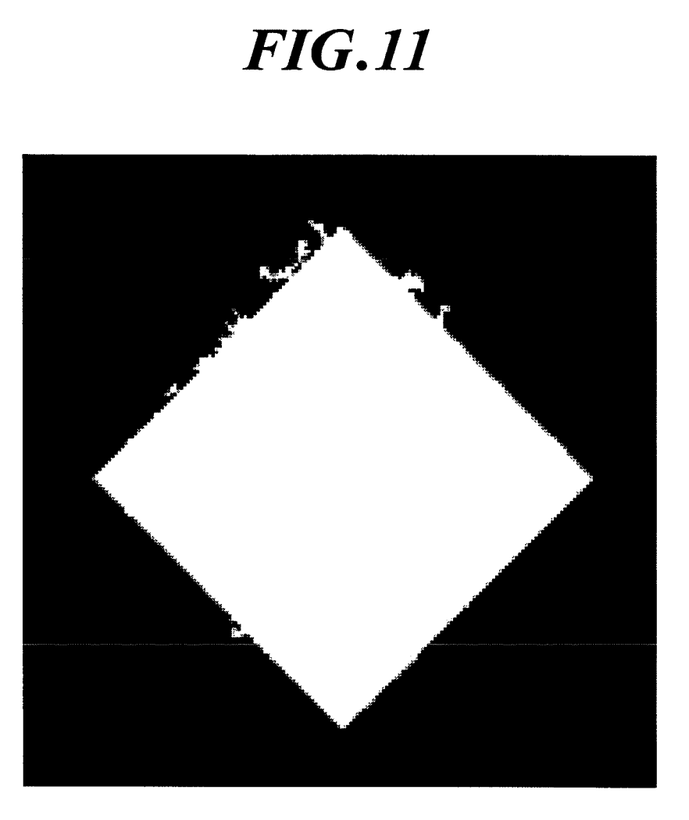
FIG. 11 shows an example of an image obtained by correcting the binarized image shown in FIG. 10.

Next, the CPU 61 performs correction on the image data binarized at Step S263 (Step S264). The correction is processing to correct the binarized image data in such a way that pixels of the binarized image data having a small curvature, the pixels corresponding to the indentation region, form a closed region. The correction is performed because, when the curvature image data is binarized at Step S263, as shown in FIG. 10, the pixels having a small curvature, the pixels corresponding to the indentation region, are sometimes dispersed. More specifically, first, the CPU 61 extracts a highlight region E1 (corresponding to the apex of the indenter 14a) formed near the center of the image by utilizing the fact that points in the indentation region, the points corresponding to the apex and the ridgelines of the indenter 14a, have high brightness by illumination, and obtains an enclosing rectangle E2 which includes the highlight region E1 and white pixels adjacent to the highlight region E1. Then, the CPU 61 divides the enclosing rectangle E2 into quadrants, and counts the number of white pixels of each quadrant. Next, the CPU 61 excludes two quadrants, one having the largest number of white pixels among the quadrants, and one having the smallest number of white pixels among the quadrants, and calculates an average of the number of white pixels of the remaining two quadrants. Then, the CPU 61 corrects the image data in such a way as to form a closed region, on the basis of the average of the number of white pixels and the area of the indentation region estimated from the shape of the indenter 14a. As a result of Step S264, the corrected image shown in FIG. 11 can be obtained, for example. The binarized image data corrected at Step S264 is stored in the storage section 63.

Then, similarly to Step S23 in FIG. 7, the CPU 61 generates copy data of the binarized image data, erodes and dilates the binarized image data using the copy data of the binarized image data, and then performs the distance transform on the eroded-and-dilated image data. After performing the distance transform on the eroded-and-dilated image data, the CPU 61 ends the binarization processing using a curvature image, and moves to Step S24 in FIG. 7.

Next, as shown in FIG. 5, the CPU 61 executes the indenter apex extraction program stored in the storage section 63, so as to extract an indentation-measurement-use apex (indentation apex extraction processing) for measuring the size (dimensions) of the indentation on the basis of the contours of the closed region extracted by the indentation region extraction processing performed at Step S2 (Step S3: an indentation apex extraction step). As for the indentation apex extraction processing, a well-known technology or a technology proposed by the present inventor in Japanese Patent Application No. 2011-201305 can be used. Hence, detailed description thereof is omitted.

Next, the CPU 61 executes the hardness calculation program stored in the storage section 63, so as to calculate hardness of the sample S on the basis of the indentation-measurement-use apex extracted at Step S3 (Step S4: a hardness calculation step). More specifically, the CPU 61 measures the lengths of diagonal lines of the indentation, referring to the coordinates of the indentation-measurement-apex extracted at Step S3, and calculates a hardness value of the sample S on the basis of the measured lengths of the diagonal lines.

Next, the CPU 61 executes the display control program stored in the storage section 63, so as to control the monitor 8 to display the hardness value of the sample S calculated at Step S4 (Step S5: a display control step).

As described above, the hardness tester 100 in the embodiment includes: an image pickup control section (CPU 61) which controls the CCD camera 12 to pick up an image of the surface of the sample S, to obtain picked-up image data of the surface of the sample S; an indentation region extraction section (CPU 61) which (i) binarizes the picked-up image data, (ii) erodes and dilates the binarized image data, and (iii) performs distance transform on the eroded-and-dilated image data, to extract a closed region corresponding to a shape of the indenter 14a using the distance-transformed image data; an indentation apex extraction section (CPU 61) which extracts an indentation-measurement-use apex on the basis of the extracted closed region, the apex being used to measure the dimension of the indentation; and a hardness calculation section (CPU 61) which calculates the hardness of the sample S on the basis of the extracted apex, wherein the indentation region extraction section determines on the basis of the binarized image data whether an indentation region candidate is extracted, and when determining that the indentation region candidate is not extracted, (i) obtains curvature image data on the basis of a brightness value of the picked-up image data, (ii) binarizes the obtained curvature image data, and (iii) erodes and dilates the binarized curvature image data.

Accordingly, even if, like the sample S undergoing the etching processing, the indentation region candidate cannot be extracted from the binarized image data, the closed region corresponding to the shape of the indenter 14a can be extracted by obtaining the curvature image data on the basis of the brightness values of the picked-up image data, and binarizing the obtained curvature image data. Hence, an indentation region can be extracted even from image data of a sample undergoing the etching processing. Furthermore, because it is not necessary to obtain two image data of the surface of the sample S, the problem caused by the image pickup position being shifted can be prevented from arising. Consequently, an indentation region can be extracted correctly. Furthermore, because it is not necessary to obtain two image data of the surface of the sample S, an indentation region can be extracted by simple processing.

In particular, in the hardness tester 100 in the embodiment, the indentation region extraction section performs Gaussian filtering on the brightness value of the picked-up image data of the surface of the sample S, calculates a derivative of the Gaussian-filtered image data, calculates a Hessian matrix on a pixel basis using the calculated derivative, and obtains the curvature image data having an absolute value of the calculated Hessian matrix as a pixel value. Accordingly, a test result with high accuracy and high reliability can be obtained.

Furthermore, in the hardness tester 100 in the embodiment, the indentation region extraction section determines whether shading correction is necessary referring to the picked-up image data of the surface of the sample S, and when determining that the shading correction is necessary, performs the shading correction on the picked-up image data thereof. Accordingly, even if the obtained image data of the surface of the sample S has uneven brightness caused by the properties of an optical system and/or an image pickup system, the shading correction is performed automatically, and hence influence of the uneven brightness on a test result can be eliminated.

In the above, an embodiment of the present invention is described in detail. However, the present invention is not limited to the embodiment, and hence can be appropriately modified without departing from the scope of the present invention.

For example, in the above, by obtaining the curvature image data on the basis of the brightness values of the image data of the surface of the sample S, and binarizing the curvature image data, a flat part where a curvature is less than a predetermined value (a threshold value) is extracted as the indentation region. Then, in the embodiment, by the correction at Step S264 and/or the erosion and the dilation, the indentation region is corrected in such a way that a region (the flat part) where a curvature is less than a predetermined value becomes the closed region corresponding to the shape of the indenter 14a. However, this is not a limit. The indentation region may be corrected by using other well-known correction processing.

In the embodiment, the monitor 8 is controlled to display the hardness value of the sample S calculated at Step S4 (the hardness calculation step) in FIG. 5. However, this is not a limit. For example, a speaker or the like which can output audio may be provided, and the calculated hardness value of the sample S may be outputted by audio.

In the embodiment, the image data binarized at Step S23 in FIG. 7 and the binarized image data corrected at Step S264 in FIG. 8 are stored in the storage section 63. However, this is not a limit. For example, these image data may be stored in the RAM 62.

In the embodiment, the hardness tester 100 is a Vickers hardness tester including the indenter 14a in the shape of a rhombic pyramid. However, this is not a limit. The present invention can be applied to, for example, a Knoop hardness tester having an indenter in the shape of a rhombic pyramid, which is the same as the Vickers hardness tester, or a Brinell hardness tester having a spherical indenter.

In addition, detailed configurations and operations of the components of the hardness tester 100 can also be appropriately modified without departing from the scope of the present invention.

The entire disclosure of Japanese Patent Application No. 2011-251247 filed on Nov. 17, 2011, including the description, claims, drawings, and abstract, is incorporated herein by reference in its entirety.

What is claimed is:

1. A hardness tester which applies a predetermined test force with an indenter to a surface of a sample placed on a sample support to form an indentation, and measures a dimension of the indentation to measure hardness of the sample, the hardness tester comprising:
    an image pickup control section which controls an image pickup section to pick up an image of the surface of the sample, to obtain picked-up image data of the surface of the sample;
    an indentation region extraction section which (i) binarizes the picked-up image data, (ii) erodes and dilates the binarized image data, and (iii) performs distance transform on the eroded-and-dilated image data, to extract a closed region corresponding to a shape of the indenter using the distance-transformed image data;
    an indentation apex extraction section which extracts an indentation-measurement-use apex on the basis of the extracted closed region, the apex being used to measure the dimension of the indentation; and
    a hardness calculation section which calculates the hardness of the sample on the basis of the extracted apex, wherein
    the indentation region extraction section determines on the basis of the binarized image data whether an indentation region candidate is extracted, and when determining that the indentation region candidate is not extracted, (i) obtains curvature image data on the basis of a brightness value of the picked-up image data, (ii) binarizes the obtained curvature image data, and (iii) erodes and dilates the binarized curvature image data.

2. The hardness tester according to claim 1, wherein the indentation region extraction section performs Gaussian filtering on the brightness value of the picked-up image data, calculates a derivative of the Gaussian-filtered image data, calculates a Hessian matrix on a pixel basis using the calculated derivative, and obtains the curvature image data having an absolute value of the calculated Hessian matrix as a pixel value.

3. The hardness tester according to claim 2, wherein the indentation region extraction section determines whether shading correction is necessary referring to the picked-up image data, and when determining that the shading correction is necessary, performs the shading correction on the picked-up image data.

4. The hardness tester according to claim 3 further comprising a display control section which controls a display section to display the calculated hardness of the sample.

5. The hardness tester according to claim 2 further comprising a display control section which controls a display section to display the calculated hardness of the sample.

6. The hardness tester according to claim 1, wherein the indentation region extraction section determines whether shading correction is necessary referring to the picked-up image data, and when determining that the shading correction is necessary, performs the shading correction on the picked-up image data.

7. The hardness tester according to claim 6 further comprising a display control section which controls a display section to display the calculated hardness of the sample.

8. The hardness tester according to claim 1 further comprising a display control section which controls a display section to display the calculated hardness of the sample.

9. A hardness tester which applies a predetermined test force with an indenter to a surface of a sample placed on a sample support to form an indentation, and measures a dimension of the indentation to measure hardness of the sample, the hardness tester comprising:
    an image pickup control section which controls an image pickup section to pick up an image of the surface of the sample, to obtain picked-up image data of the surface of the sample;
    an indentation region extraction section which obtains curvature image data on the basis of a brightness value of the picked-up image data, and extracts a flat part where a curvature is less than a predetermined value as an indentation region referring to the obtained curvature image data; and
    a hardness calculation section which calculates the hardness of the sample on the basis of the indentation region.

10. A hardness test method which applies a predetermined test force with an indenter to a surface of a sample placed on a sample support to form an indentation, and measures a dimension of the indentation to measure hardness of the sample, the hardness test method comprising:
    controlling an image pickup to pick up an image of the surface of the sample, to obtain picked-up image data of the surface of the sample;
    extracting by (i) binarizing the picked-up image data, (ii) eroding and dilating the binarized image data, and (iii) performing distance transform on the eroded-and-dilated image data, to extract a closed region corresponding to a shape of the indenter using the distance-transformed image data;
    extracting an indentation-measurement-use apex on the basis of the extracted closed region, the apex being used to measure the dimension of the indentation; and
    calculating the hardness of the sample on the basis of the extracted apex, wherein
    in the extracting, whether an indentation region candidate is extracted is determined on the basis of the binarized image data, and when that the indentation region candidate is not extracted is determined, (i) curvature image data is obtained on the basis of a brightness value of the picked-up image data, (ii) the obtained curvature image data is binarized, and (iii) the binarized curvature image data is eroded and dilated.

11. A hardness test method which applies a predetermined test force with an indenter to a surface of a sample placed on a sample support to form an indentation, and measures a dimension of the indentation to measure hardness of the sample, the hardness test method comprising:
    controlling an image pickup to pick up an image of the surface of the sample, to obtain picked-up image data of the surface of the sample;
    obtaining curvature image data on the basis of a brightness value of the picked-up image data, and extracting a flat part where a curvature is less than a predetermined value as an indentation region referring to the obtained curvature image data; and calculating the hardness of the sample on the basis of the indentation region.

* * * * *